United States Patent [19]

Imazaki et al.

[11] Patent Number: 4,526,932

[45] Date of Patent: Jul. 2, 1985

[54] ANTIFOULING AGENT

[75] Inventors: Hideyuki Imazaki, Osaka; Kazuhiko Sakamoto, Suita, both of Japan

[73] Assignee: Nitto Kasei Co., Ltd., Osaka, Japan

[21] Appl. No.: 482,558

[22] Filed: Apr. 6, 1983

[30] Foreign Application Priority Data

Apr. 6, 1982 [JP] Japan .................................. 57-57862
Apr. 13, 1982 [JP] Japan .................................. 57-62204

[51] Int. Cl.³ ............................................. C08F 8/42
[52] U.S. Cl. .............................. 525/326.7; 525/326.8; 525/326.9; 525/328.2; 525/370; 525/359.1
[58] Field of Search ............... 525/326.7, 326.8, 326.9, 525/328.2

[56] References Cited

PUBLICATIONS

C.A. 59535v "N-Vinylindole and Organic Halogen--Containing Electron-Acceptor Charge Transfer Complexes" vol. 83, 1975.

C.A. 81580r "Infrared and U.V. Spectra of Complexes of N-Vinylazoles with Haloorganostannanes", vol. 80, 1974.

*Primary Examiner*—Bernard Lipman
*Attorney, Agent, or Firm*—Wenderoth, Lind & Ponack

[57] ABSTRACT

An antifouling agent comprising as an antifouling component a substantially linear triorganotin-containing copolymer containing (a) at least one kind of N-coordinated triorganotin-containing recurring units of the formula (Ia) or (Ib) represented in the specification and (b) comonomer recurring units derived from at least one ethylenic vinyl compound as a comonomer. The antifouling agent is applied to a structure which is needed to be protected from fouling organisms to form a film of the copolymer on the structure.

10 Claims, No Drawings

ANTIFOULING AGENT

This invention relates to an anti-fouling agent comprising as an anti-fouling component a triorganotin-containing copolymer having N-coordinated-triorganotin-recurring units in the main polymer chain.

Marine algae such as green layer (*Ulva lactuca*), Enteromorpha, and brown algae, and fouling organisms such as acorn barnacle (Balanus), Serpulae, oysters, ascidian and Bryozoa adhere to the bottoms of ships, fishing nets such as cultivation nets and fixed nets, or general underwater structures to do various damages. When these marine fouling organisms adhere to a ship's bottom, friction resistance between the hull and sea water increases and results in a decrease in cruising speed and an increase in fuel consumption. On the other hand, fouling organisms adhering to a fishing net block up the meshes to hamper the passing of sea water and reduce the growth and harvest of cultured fish. Sometimes, the fishing net which has acquired increased resistance owing to the adhering organisms will be swept away by the sea current.

In order to prevent or reduce such damages, it is the current practice to coat the surfaces of substrate materials to be exposed to fresh water or sea water with various antifouling agents or paints, and in particular, it is considered important from the viewpoint of economy and resource saving to prevent adhesion of antifouling organisms to the bottom of a huge tanker over an extended period of time by coating it with an antifouling paint.

Triorganotin compounds such as tributyltin compounds (oxide, chloride, fluoride) or triphenyltin compounds (hydroxide, chloride, fluoride) have heretofore been used to prevent adhesion of antifouling organisms. Since, however, these compounds have strong toxicity, they may cause skin irritation or eruption during the production and application of paints. Furthermore, their antifouling properties cannot be maintained over an extended period of time because triorganotin compounds dissolve in sea water in the relatively early stage, and it is difficult to control their dissolving.

In an attempt to remedy the aforesaid defects, there was proposed as an antifouling agent a triorganotin-containing polymer in which a triorganotin moiety as an antifouling ingredient is fixed as a polymer of a compound of the following formula

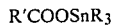

wherein R is a lower alkyl or phenyl group, and R' is a polymerizable group selected from the group consisting of the vinyl, α-methylvinyl and vinylphenyl radicals (U.S. Pat. No. 3,167,473). An antifouling agent comprising as an antifouling component a triorganotin-containing polymer in which a triorganotin moiety is fixed as a carboxylate is disclosed also in British Pat. Nos. 1,062,324 and 1,408,327.

These antifouling agents in which the triorganotin moiety is fixed as a carboxylate have the defect that they increase in viscosity and become a gel during storage.

For example, this phenomenon is especially pronounced with a triphenyltin-containing polymer, and in an extreme case, gellation occurs during the polymerization process and a stable polymer is difficult to obtain. With long-term antifouling marine paints, a tributyltin-containing polymer is used together with a copper compound such as cuprous oxide in order to increase antifouling activity and maintain it over long periods of time. Hence, gellation is accelerated during storage of these marine paints, and sometimes, the paints become useless. For this reason, it has been necessary to prevent gellation during storage by adding a stabilizer, or by storing the polymer component and the copper compound component separately and mixing them just before application. These methods, however, have not offered an essential solution to the above problem. Another defect is that it is difficult to produce a triphenyltin-containing polymer in which the triphenyltin moiety is fixed as a carboxylate, which is particularly effective against algae.

It is an object of this invention therefore to provide a novel antifouling agent comprising a novel antifouling component.

Another object of this invention is to provide an antifouling agent comprising a novel antifouling component, in which a triorganotin compound as the antifouling component is fixed by forming a coordination bond with the nitrogen atom possessed by a pendant group of a polymer.

Still another object of this invention is to provide a novel antifouling agent containing as an antifouling component a polymer which by itself can form an intimately adhering, tough coated film on an article to be coated.

Yet another object of this invention is to provide a novel antifouling agent which has long-term storage stability even in the presence of a copper compound such as cuprous oxide.

A further object of this invention is to provide a novel antifouling agent which when coated on a structure to be dipped in sea water, can keep the coated article protected from antifouling marine organisms over an extended period of time.

An additional object of this invention is to provide an antifouling agent containing a novel, triphenyltin-containing polymeric antifouling component which is particularly suitable for protecting a structure from fouling by algae.

Other objects and advantages of this invention will become apparent from the following description.

According to this invention, the above objects and advantages are achieved by an antifouling agent comprising as an antifouling component a substantially linear triorganotin-containing copolymer containing (a) at least one kind of N-coordinated triorganotin-containing recurring units of the formula

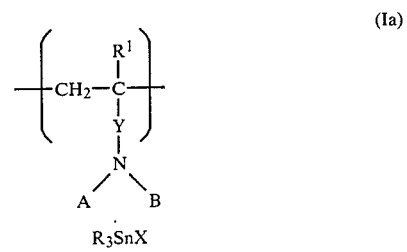

(Ia)

wherein $R^1$ represents a hydrogen atom, a methyl group, an ethyl group or a halogen atom; Y represents a bond, an alkylene group having 1 to 12 carbon atoms, a phenylene group, a group of the formula

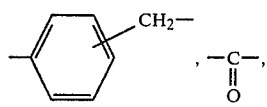

or a group of the formula

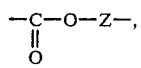

—O—Z—, or —S—Z— in which Z represents an alkylene group having 2 to 12 carbon atoms or a group of the formula

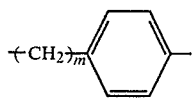

in which m is an integer of 1 to 8; A and B either (i) independently from each other represent a hydrogen atom, an alkyl group having 1 to 18 carbon atoms, a cycloalkyl group, an aryl group, an aralkyl group, a hydroxyalkyl group having 2 to 4 carbon atoms, an alkoxyalkyl group having 3 to 12 carbon atoms, or a group of the formula

in which $R^3$ represents an alkyl group having 1 to 18 carbon atoms, or an aryl group, or (ii) are bonded to each other together with the nitrogen atom to which they are bonded, to form a 5- or 6-membered heterocyclic ring; groups R are identical or different and each represents an alkyl group having 1 to 8 carbon atoms, a cycloalkyl group, an aryl group, or an aralkyl group; and X represents a halogen atom, or

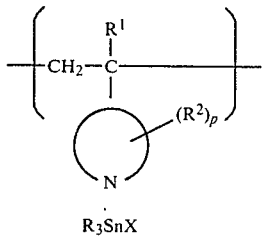

$R_3SnX$ wherein $R^1$, R and X are as defined with regard to formula (Ia); $R^2$ represents a hydrogen atom, a methyl group, an ethyl group or a halogen atom; p is an integer of from 1 to 4; and the symbol

represents a 5- or 6-membered heterocyclic ring bonded through a ring-member atom other than the nitrogen atom to the carbon atom to which $R^1$ is bonded, and (b) comonomer recurring units derived from at least one ethylenic vinyl compound as a comonomer.

The antifouling agent of this invention contains as an antifouling component a substantially linear triorganotin-containing copolymer containing the recurring units (a) and (b) specified above. The triorganotin-containing copolymer is very characteristic in that it contains the recurring units (a), i.e. N-coordinated-triorganotin-containing recurring units in which the triorganotin-containing compound is coordinated with the nitrogen atom in the polymer. The N-coordinated triorganotin-containing recurring units are represented by formula (Ia) or (Ib) above. It will be seen that formulae (Ia) and (Ib) are common in that they have the portion

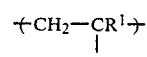

forming the main chain of the polymer, and the triorganotin compound $R_3SnX$ is coordinated with the nitrogen atom of the pendant group of the polymer chain.

In formula (Ia), $R^1$ represents a hydrogen atom, a methyl group, an ethyl group or a halogen atom. Examples of the halogen atom are fluorine, chlorine and bromine. Chlorine is preferred.

Y represents a bond, an alkylene group having 1 to 12 carbon atoms, a phenylene group

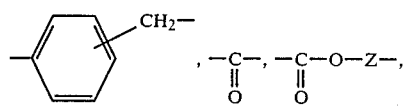

—O—Z—, or —S—Z— wherein Z represents an alkylene group having 2 to 12 carbon atoms, or a group of the formula

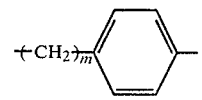

in which m is an integer of 1 to 8.

The alkylene group having 1 to 12 carbon aroms may be linear or branched, and preferably has 1 to 4 carbon atoms. Specific examples of the alkylene group are methylene, dimethylene, trimethylene, 1,2-propylene, tetramethylene, pentamethylene, hexamethylene, octamethylene, decamethylene and dodecamethylene.

The alkylene group having 2 to 12 carbon atoms representing Z may also be linear or branched, and preferably has 2 to 4 carbon atoms. Specific examples are the same as those given above for the alkylene group having 1 to 12 carbon atoms, excepting methylene. The group

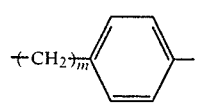

is preferably one in which m is 1 to 3. Specific examples thereof are self-evident.

Preferably, Y represents a bond, an alkylene group having 1 to 4 carbon atoms, a phenylene group,

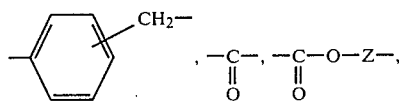

—O—Z—, or —S—Z— (wherein Z is an alkylene group having 2 to 4 carbon atoms or a group of the formula

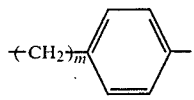

in which m is 1 to 3, preferably 1). Especially preferably, Y is a bond,

a phenylene group,

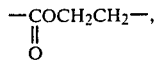

and —O—CH$_2$—CH$_2$—. It will be understood that when Y is a bond, the nitrogen atom to which A and B are bonded is directly bonded to the carbon atom to which R$^1$ is bonded in formula (Ia).

A and B either (i) independently from each other represent a hydrogen atom, an alkyl group having 1 to 18 carbon atoms, a hydroxyalkyl group having 2 to 4 carbon atoms, a cycloalkyl group, an aryl group, an aralkyl group, an alkoxyalkyl group having 3 to 12 carbon atoms, or a group of the formula

in which R$^3$ is an alkyl group having 1 to 18 carbon atoms, or an aryl group; or (ii) are bonded to each other and, together with the nitrogen atom to which they are bonded, form a 5- or 6-membered heterocyclic ring.

The alkyl group having 1 to 18 carbon atoms may be linear or branched, and preferably has 1 to 8 carbon atoms. Examples of the alkyl group include methyl, ethyl, propyl, isopropyl, butyl, isobutyl, t-butyl, pentyl, hexyl, octyl, decyl, dodecyl, hexadecyl and octadecyl.

Examples of the hydroxyalkyl group having 2 to 4 carbon atoms are hydroxyethyl, hydroxypropyl and hydroxybutyl. Hydroxyalkyl groups having 2 or 3 carbon atoms are preferred.

The cycloalkyl group is preferably a 5- or 6-membered cycloalkyl group such as cyclohexyl, cyclopentyl and cycloheptyl. Phenyl and naphthyl groups are preferred as the aryl group. The aryl group may be substituted by a lower alkyl group such as methyl or ethyl. Unsubstituted phenyl and naphthyl groups are preferred as the aryl group. Preferred aralkyl groups are phenylalkyl and naphthylalkyl groups, especially the phenylalkyl groups such as benzyl, α-phenethyl and β-phenethyl.

The alkoxyalkyl group having 3 to 12 carbon atoms is preferably such that the alkoxy moiety has 1 to 12 carbon atoms and the alkyl moiety has 2 to 4 carbon atoms. Preferred alkoxyalkyl groups are those having 3 to 8 carbon atoms, especially those composed of an alkoxy moiety having 1 to 4 carbon atoms and an alkyl moiety having 2 to 4 carbon atoms. Examples of the alkoxyalkyl groups are methoxyethyl, methoxypropyl, methoxybutyl, ethoxyethyl, ethoxypropyl, ethoxybutyl, propoxyethyl, isopropoxyethyl, butoxyethyl and t-butoxyethyl.

In the acyl group of the formula

R$^3$ is an alkyl group having 1 to 18 carbon atoms, or an aryl group. Specific examples of the alkyl group having 1 to 18 carbon atoms and the aryl group are those already given hereinabove. Preferred acyl groups are those of the formula

wherein R$^{31}$ is an alkyl group having 1 to 8 carbon atoms, a phenyl group, a tolyl group, or a naphthyl group. Specific examples include acetyl, propionyl, butyryl, valeryl, caproyl, caprylyl, capryl, lauryl, palmityl, stearyl, benzoyl, tolylcarbonyl and naphthylcarbonyl.

In the case of (i), A and B may be identical or different, and preferably the group

represents an amino group, a dialkylamino group, an N-acyl-N-alkylamino group, an N-alkyl-N-arylamino group or N-acyl-N-arylamino group.

In the case of (ii), A and B may represent a 5- or 6-membered heterocyclic ring together with the nitrogen atom to which they are bonded. The heterocyclic ring may include another ring-member hetero atom in addition to the nitrogen atom, or they may be substituted, or fused with another ring. Preferably, the heterocyclic ring formed by A and B does not include another ring-member hetero atom in addition to the nitrogen atom, or contains an oxygen or sulfur atom as the ring-member hetero atom in addition to the nitrogen atom. Especially preferred is a 6-membered heterocyclic ring in which the group

does not contain another ring-member hetero atom in addition to the nitrogen atom, or contains an oxygen atom as the ring-member hetero atom in addition to the nitrogen atom.

Examples of such a heterocyclic ring group are as follows:

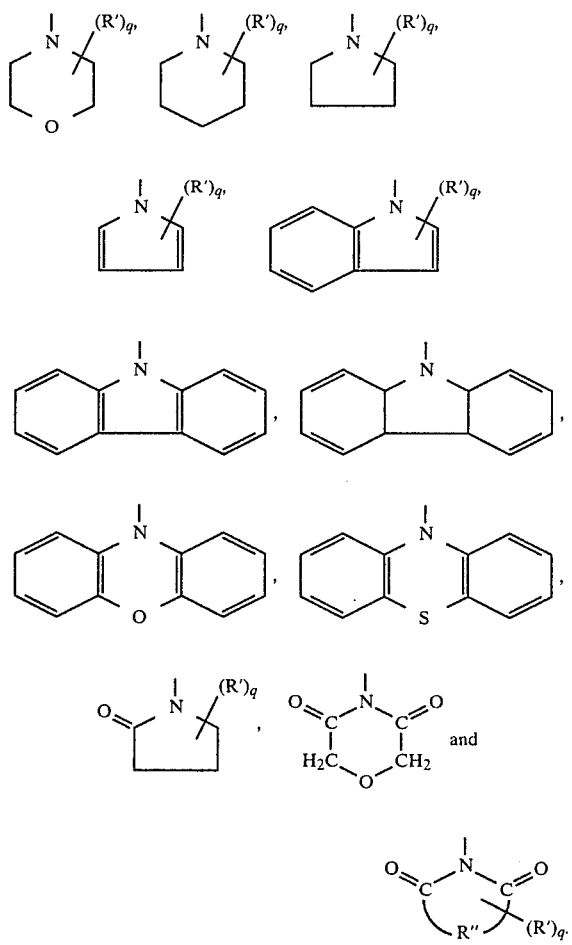

In these formulae, R' represents a hydrogen atom, an alkyl group having 1 to 8 carbon atoms, an aryl group or an aralkyl group; R" represents an alkylene group having 2 or 3 carbon atoms, a cyclohexylene group, or a phenylene group; and q represents an integer of 1 to 5.

Groups R are identical or different and each represents an alkyl group having 1 to 8 carbon atoms, a cycloalkyl group, an aryl group or an aralkyl group. The alkyl group having 1 to 8 carbon atoms may be linear or branched, preferably linear. Preferred alkyl groups contain 1 to 5 carbon atoms. Specific examples include methyl, ethyl, propyl, isopropyl, butyl, pentyl, hexyl and octyl. Cyclopentyl and cyclohexyl groups are the preferred cycloalkyl groups. The cyclohexyl group is especially preferred. The aryl group may be substituted, but is preferably unsubstituted. Examples of the aryl group are phenyl and naphthyl groups. The aralkyl group may be substituted at the phenyl nucleus, but is preferably unsubstituted. Preferred aralkyl groups are phenylalkyl and naphthylalkyl groups, especially benzyl, α-phenethyl, and β-phenethyl.

X represents a halogen atom such as chlorine, bromine or iodine. The chlorine atom is especially preferred.

In formula (Ib), $R^1$, R and X are the same as defined in formula (Ia). Preferred species and specific examples of these are as given hereinabove.

In formula (Ib), symbol

represents a 5- or 6-membered heterocyclic ring bonded at a ring-member atom other than the nitrogen atom to the carbon atom to which $R^1$ is bonded; $R^2$ represents a hydrogen atom, a methyl group, an ethyl group, or a halogen atom; and p is an integer of 1 to 4. The halogen atom is, for example, fluorine, chlorine, bromine or iodine. The 5- or 6-membered heterocyclic ring represented by the above symbol may be fused with another ring such as a benzene ring. It is preferably a 6-membered heterocyclic ring which does not contain another ring-member hetero atom than the nitrogen atom. Examples of the heterocyclic ring represented by the above symbol when $R^2$ is a hydrogen atom are as follows:

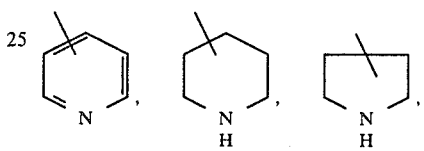

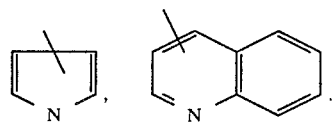

A method for producing the substantially linear triorganotin-containing copolymer as an antifouling component of the antifouling agent of the present invention (to be referred to hereinafter as the triorganotin-containing copolymer of the invention) will be described below in detail. By the following description, the recurring units (a) and (b) constituting the triorganotin-containing copolymer will be understood more specifically.

The triorganotin-containing copolymer of this invention can usually be produced by any of the following two methods. Conceptually, a first method comprises first producing a polymer not containing a triorganotin compound, and then allowing a triorganotin compound to act upon the resulting polymer. A second method comprises preparing a triorganotin-containing monomer and polymerizing it.

The first method comprises copolymerizing a polymerizable unsaturated compound having a nitrogen atom at a pendant group represented by the following formula

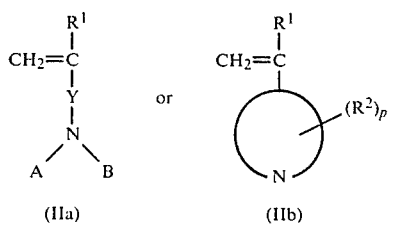

wherein $R^1$, Y, A, B, $R^2$, p and symbol

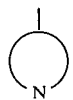

are as defined hereinabove. with another ethylenic vinyl compound copolymerizable with it, and allowing a triorganotin compound represented by the following formula $$R_3SnX$$

wherein R and X are as defined hereinabove, to act directly on the resulting copolymer.

Examples of the polymerizable unsaturated compound of formula (IIa) are shown below. For simplicity of exemplification, compounds of formula (IIa) in which Y is a bond will first be exemplified, and then compounds of formula (IIa) in which Y is another group will be exemplified.

Examples of the compounds in which Y is a bond include N-vinylamines such as N-vinyl-N-ethylamine, N-vinyl-N-n-butylamine, N-vinyl-N-n-dodecylamine, N-vinyl-N-cyclohexylamine, N-vinyl-N,N-dimethylamine, N-vinyl-N,N-diethylamine, N-vinyl-N-methyl-N-phenylamine, N-vinyl-N-phenylamine, N-vinyl-N-phenyl-N-β-naphthylamine, N-vinyl-N-p-tolyl-N-α-naphthylamine, N-vinylpyrrole, N-vinylindole, N-vinyl-α-methylindole, N-vinyl-carbazole, N-vinyl-1,2,3,4-tetrahydrocarbazole, N-vinylphenothiazine, N-vinylnaphthophenothiazine, N-vinylmorpholine, n-vinylpiperidine, N-vinylphenoxazine and V-vinylpyrrolidine; N-vinylamides such as N-vinylacetamide, N-vinyl-N-methylacetamide, N-vinylacetanilide, N-vinyl-N-methylbenzamide, N-vinylpyrrolidone, N-vinyl-3-methylpyrrolidone, N-vinyl-5-methylpyrrolidone, N-vinyl-5-phenylpyrrolidone and N-vinyl-3-benzylpyrrolidone; and N-vinylimides such as N-vinylsuccinimide, N-vinylglutarimide, N-vinyldiglycolimide, N-vinylphthalimide, and N-vinyltetrahydrophthalimide.

Examples of the compounds of formula (IIa) in which Y is another group include aminoolefins such as allylamine, N-allyl-N-methylamine, N-allyl-N,N-dimethylamine, N-allyl-N-ethylamine, N-allyl-N,N-diethylamine, N-methallylamine, N-methallyl-N-methylamine, N-methallyl-N-ethylamine, N-methallyl-N-methyl-N-ethylamine, N-methallyl-N-phenyl-N-ethylamine, 1-ethylamino-3-butene, 1-dimethylamino-4-pentene, 1-diethylamino-4-pentene, 12-dodecenylamine, N-allyl-N,N-dibenzylamine, N-allyl-N-ethyl-N-phenylamine, N-allylmorpholine, N-methallylmorpholine, N-allylpyrrole, N-allylindole, N-methallylpiperidine, N-methallylpyrrolidine, N-methallylpyrrolidone and N-allylcarbazole, N-allylaniline, N-allyl-N-methylaniline, aminostyrenes such as o-aminostyrene, m-aminostyrene, p-aminostyrene, p-dimethylaminostyrene, p-diethylaminostyrene, o-vinylbenzylamine, p-N,N-dimethylaminomethylstyrene, N-(o-vinylbenzyl)pyrrolidine, N-(p-vinylbenzyl)morpholine, N-(o-vinylbenzyl)piperidine, N-(o-vinylbenzyl)pyrrole, N-(p-vinylbenzyl)indole, and N-(o-vinylbenzyl)carbazole; olefin amides such as acrylamide, methacrylamine, N-methacrylamide, N,N-dimethylacrylamide, N-ethylacrylamide, N,N-diethylacrylamide, N,N-dimethylmethacrylamide, N,N-diethylmethacrylamide, N-ethyl-N-phenylacrylamide, N-methylolacrylamide, N-octylacrylamide, N-methoxymethylacrylamide, N-2,2-dimethyl-propoxymethylacrylamide, N,N-diethanolacrylamide, N,N-diethanol methacrylamide, diacetone acrylamide, N-methylacrylanilide, acryloylmorpholine, methacryloylpiperidine, acryloylpyrrolidine, methacryloylmorpholine, acryloylindole, acryloylcarbazole, and methacryloyltetrahydrocarbazole; aminoacrylates or aminomethacrylates such as N-methylaminoethyl acrylate, N-ethylaminoethyl acrylate, N,N-dimethylaminoethyl acrylate, N,N-diethylaminoethyl acrylate, N-methylaminoethyl methacrylate, N,N-dimethylaminoethyl methacrylate, N-ethylaminoethyl methacrylate, N,N-diethylaminoethyl methacrylate, N,N-dimethylaminopropyl methacrylate, N-t-butylaminoethyl acrylate, N,N-diethylaminohexyl methacrylate, N-(methoxymethyl)aminoethyl acrylate, N-(ethoxyethyl)aminoethyl methacrylate, N-methyl-N-phenylaminoethyl methacrylate, p-N,N-diethylaminobenzyl methacrylate, O-N,N-dimethylaminophenethyl methacrylate, β-morpholinoethyl methacrylate, γ-morpholinopropyl acrylate, β-pyrrolidylethyl methacrylate, and β-carbazoylethyl acrylate; vinyl ethers such as N,N-dimethylaminoethylvinyl ether, N,N-diethylaminoethylvinyl ether, 3-aminopropylvinyl ether, 5-aminopentylvinyl ether, 8-aminooctylvinyl ether, 10-aminodecylvinyl ether, 2-aminobutylvinyl ether, N-t-butylaminoethylvinyl ether, N-methylaminoethylvinyl ether, N-2-ethylhexylaminoethylvinyl ether, (N-β-hydroxyethyl-N-methyl)aminoethylvinyl ether, N,N-dihydroxyethylaminoethylvinyl ether, N,N-diphenylaminoethylvinyl ether, α-pyrrolidylethylvinyl ether, β-morpholinoethylvinyl ether, β-piperidinoethylvinyl ether, γ-morpholinopropylvinyl ether and β-carbazoylethylvinyl ether; and aminovinyl sulfies such as aminoethylvinyl sulfide, N,N-dimethylaminoethylvinyl sulfide, 5-aminopentylvinyl sulfide, N-ethyl-N-phenylaminopropylvinyl sulfide and N,N-diethylaminoethylvinyl sulfide.

Examples of the nitrogen-containing polymerization unsaturated compound represented by formula (IIb) are 2-vinylpyridine, 3-vinylpyridine, 4-vinylpyridine, 2-vinyl-4-methylpyridine, 4-vinyl-2-methylpyridine, 2-vinylpiperidine, 4-vinylpiperidine, 4-vinyl-2-methylpiperidine, 2-vinylpyrrolidine, 3-vinylpyrrolidine, 3-vinylpyrrole, and 2-vinylquinoline.

The other ethylenic vinyl compound to be copolymerized with the nitrogen-containing polymerizable unsaturated compound of formula (IIa) or (IIb) may be any other ethylenic vinyl compound which can be copolymerized with the polymerizable unsaturated compound. Examples of the other ethylenic vinyl compound are acrylic compounds, vinyl compounds having a functional group, vinyl-type hydrocarbon compounds, triorganotin salts of polymerizable unsaturated carboxylic acids, polymerizable unsaturated dicarboxylic acids, and anhydrides of these dicarboxylic acids.

Examples of the acrylic compounds are compounds of the following formula

wherein $R^4$ represents a hydrogen atom, a substituted or unsubstituted hydrocarbon group having 1 to 20 carbon atoms, and $R^5$ represents a hydrogen atom, a halogen atom or an alkyl group having 1 to 6 carbon atoms.

Examples of the compounds include acrylic acids or methacrylic acids, such as acrylic acid, methacrylic acid, α-ethylacrylic acid and α-chloroacrylic acid; acrylic acid esters such as methyl, ethyl, propyl, butyl, amyl, hexyl, octyl, dodecyl, octadecyl, cyclopentyl, cyclohexyl, phenyl and benzyl; methacrylic acid esters such as methyl, ethyl, butyl, hexyl, octyl and dodecyl methacrylates; and α-substituted acrylic acid esters such as esters of α-chloroacrylic acid and butyl α-ethylacrylate. Especially preferred acrylic compounds are methyl acrylate, ethyl acrylate, n-butyl acrylate, 2-ethylhexyl acrylate, n-octyl acrylate, methyl methacrylate, ethyl methacrylate, n-butyl methacrylate, n-octyl methacrylate and n-dodecyl methacrylate. The compounds may be used singly or as a mixture of two or more.

Examples of the vinyl compounds having a functional group are those of the following formula

(IVb)

wherein Q represents a halogen atom, —CN, —OR*, —SR*, —COR*, or —OCOR* in which R* represents a substituted or unsubstituted hydrocarbon group having 1 to 20 carbon atoms; and Q' represents a hydrogen atom, a halogen atom or an alkyl group having 1 to 6 carbon atoms.

Examples of these compounds include vinyl halides such as vinyl chloride and vinylidene chloride; acrylonitriles such as acrylonitrile and methacrylonitrile; vinyl ethers such as methyl vinyl ether, ethyl vinyl ether, β-chloroethyl vinyl ether, butyl vinyl ether, octyl vinyl ether, decyl vinyl ether, lauryl vinyl ether, phenyl vinyl ether, O-methylphenyl vinyl ether, benzyl vinyl ether and β-naphthyl vinyl ether; vinyl thioethers such as methyl vinyl sulfide, divinyl sulfide and butyl vinyl sulfide; vinyl ketones such as methyl vinyl ketone and phenyl vinyl ketone; and vinyl esters such as vinyl formate, vinyl acetate, vinyl propionate, vinyl butyrate, vinyl laurate, vinyl benzoate and vinyl salicylate. Especially preferred compounds are vinyl chloride, acrylonitrile, butyl vinyl ether, decyl vinyl ether, lauryl vinyl ether and vinyl acetate. These compounds can be used either singly or as a mixture of two or more.

Examples of the vinyl-type hydrocarbon compounds are compounds of the following formula

(IVc)

wherein P and P' represent a hydrocarbon atom or a hydrocarbon group having 1 to 18 carbon atoms.

Specific examples of these compounds include olefins such as ethylene, propylene, 1-butene, cyclohexene and α-pinene; dienes such as 1,3-butadiene; and styrenes such as styrene, α-methylstyrene, O-methylstyrene, m-methylstyrene and p-methylstyrene. Styrene can be cited as an especially preferred compound. These compounds may be used singly or as a mixture of two or more.

Examples of the triorganotin salt of a polymerizable unsaturated carboxylic acid are compounds of the following formula

(IVd)

wherein $R^6$ represents a hydrogen atom or a group of the formula —$COOR^9$ and $R^7$ represents a hydrogen atom, a lower alkyl group or a group of the formula —$CH_2COOR^{10}$, and $R^8$, $R^9$ and $R^{10}$ are identical or different and each represents a triorganotin group.

Specific examples of the compounds of formula (IVd) are tripropyltin methacrylate, tributyltin methacrylate, triamyltin methacrylate, triphenyltin methacrylate, tripropyltin acrylate, tributyltin acrylate, triamyltin acrylate, triphenyltin acrylate, bis(tripropyltin)itaconate, bis(tributyltin)itaconate, bis(tricyclohexyltin)itaconate, bis(triphenyltin)itaconate, bis(tributyltin)maleate and bis(triphenyltin)maleate. Especially preferred examples are tributyltin methacrylate, triphenyltin methacrylate, tributyltin acrylate, triphenyltin acrylate, bis(tributyltin)itaconate, bis(triphenyltin)itaconate, bis(tributyltin)maleate and bis(triphenyltin)maleate. These compounds are used either singly or as a mixture of two or more.

Examples of the polymerizable unsaturated dicarboxylic acid or its anhydride include maleic acid, itaconic acid, maleic anhydride, and itaconic anhydride. Itaconic acid and maleic anhydride are preferred.

The copolymerization of the nitrogen-containing polymerizable unsaturated compound of formula (IIa) or (IIb) with the other ethylenic vinyl compound copolymerizable with it can be carried out in accordance with a method known per se, for example, in the presence of a suitable polymerization catalyst such as a radical catalyst by bulk polymerization, solution polymerization, emulsion polymerization or suspension polymerization. The solution polymerization technique is preferred because it is convenient in performing a reaction of introducing the triorganotin halide later.

The N-coordinated triorganotin-containing copolymer in accordance with this invention can be produced by treating the resulting copolymer, preferably a copolymer containing about 1 to about 95% by weight of units derived from the nitrogen-containing polymerizable unsaturated compound of formula (IIa) or (IIb) based on the total weight of these units and units derived from the other ethylenic vinyl compound, with the triorganotin compound ($R_3SnX$).

Examples of preferred triorganotin compounds ($R_3SnX$) include trimethyltin chloride, trimethyltin bromide, trimethyltin iodide, tripropyltin chloride, tripropyltin bromide, tributyltin chloride, tributyltin bromide, tributyltin iodide, triamyltin chloride, triamyltin bromide, triphenyltin chloride, triphenyltin bromide, triphenyltin iodide, tricyclohexyltin chloride, tricyclohexyltin bromide, dibutylphenyltin chloride, and diphenylethyltinchloride. Tributyltin chloride and triphenyltin chloride are especially preferred.

The treatment of the copolymer having a nitrogen atom in a pendant group obtained by the above polymerization process with the triorganotin halide can be carried out by contacting the copolymer with the triorganotin halide usually in the presence of at least one organic solvent selected, for example, from aromatic hydrocarbons such as benzene, toluene and xylene, ketones such as methyl ethyl ketone, methyl isobutyl ketone and cyclohexanone, ethers such as tetrahydrofuran, dibutyl ether and diglyme, alcohols such as isopropanol, butanol and ethyl Cellosolve, and lower fatty acid esters such as ethyl acetate, isopropyl acetate, butyl acetate, propyl butyrate, and butyl butyrate. The amount of the triorganotin halide used is preferably 0.1 to 1 mole, per nitrogen atom indicated in formula (IIa) or (IIb) contained in the copolymer.

According to the above method, the triorganotin halide and the nitrogen-containing copolymer give the N-coordinated-triorganotin-containing copolymer by forming a ligand bond between the tin atom and the nitrogen atom (ligand). Accordingly, although the N-coordinated triorganotin-containing copolymer has a high molecular weight, it may fall into a category generally called an adduct compound, a double salt or a complex compound, or a category called a coordination compound in a broad sense.

The coordination bond between the nitrogen atom of the nitrogen-containing copolymer and the tin atom of the triorganotin halide can be determined by various instrumental analyses, for example by the shifting of absorption bands of Sn-C and Sn-Cl in an infrared absorption spectrum, or by analytical techniques of $^{119}$Sn nuclear magnetic resonance spectroscopy or X-ray diffraction.

According to this invention, the N-coordinated triorganotin-containing copolymer of this invention may alternatively be produced directly by copolymerizing a triorganotin-containing monomer represented by the following formula

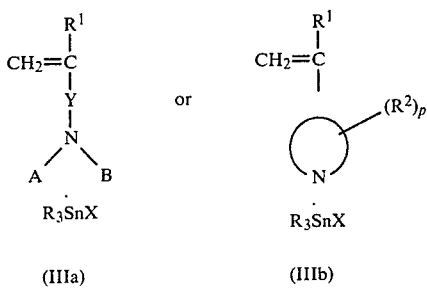

wherein $R^1$, Y, A, B, R, X, $R^2$ and p are as defined hereinabove, with an ethylenic vinyl compound copolymerizable therewith.

The compound of formula (IIIa) or (IIIb) can be easily produced by contacting the compound of formula (IIa) or (IIb) with the triorganotin halide ($R_3SnX$). The other ethylenic vinyl compound may be the same as described with regard to the first method. The polymerization can also be carried out in the same way as described with regard to the first method.

The triorganotin-containing copolymer of this invention may contain various proportions of the N-coordinated-triorganotin containing recurring units depending upon the required antifouling film formability or antifouling ability. Preferably, it may contain 10 to 80% by weight of N-coordinated-triorganotin-containing recurring units and 90 to 20% by weight of recurring units derived from the comonomer, based on the total weight of these recurring units.

Especially preferably, the triorganotin-containing copolymer of this invention consists substantially of the N-coordinated triorganotin-containing recurring units and the comonomer recurring units.

The triorganotin-containing copolymer of this invention preferably has a weight average molecular weight of 5,000 to 500,000.

The antifouling agent of this invention may include the triorganotin-containing copolymer of the invention as an antifouling component in various modes depending upon the desired antifouling purpose. For example, the triorganotin-containing copolymer of this invention may be used as a solution in the same solvent as used in the aforesaid solution polymerization, for example an organic solvent such as a hydrocarbon, ketone, ester, alcohol or ether either singly or together. Or the triorganotin-containing copolymer solution obtained by the aforesaid methods can be used directly or after dilution, as an antifouling agent.

The resulting solution of the triorganotin-containing copolymer in the organic solvent is a viscous liquid which is colorless, pale yellow or yellowish brown.

The copolymer solution can be obtained as a solvent an organic solvent solution containing usually 10 to 80% by weight, preferably 40 to 60% by weight, of the triorganotin-containing copolymer.

As required, the antifouling agent of this invention may include a dye, a pigment, a carrier, a copper compound such as cuprous oxide or cuprous rhodanate, an organotin compound, a paint adjusting agent, a toxicant dissolution controlling agent, a diluent, etc. and can be used as an antifouling agent for fishing nets, or an antifouling ship bottom paint. There is no particular restriction on the proportion of the triorganotin-containing copolymer of the invention in the antifouling agent. For example, it can be 5 to 70% by weight based on total solids.

The antifouling agent of this invention forms a good coated film on various substrates. For example, when it is coated on a wooden plate, a metal plate, or a rope or net made of synthetic fibers and dried, a coated film of the triorganotin-containing copolymer having good elasticity and adhesion is formed.

Since, in the present invention, the triorganotin-containing copolymer itself serves both as an antifouling component and a film-forming agent (varnish), other vehicles such as oil varnishes, vinyl resin varnishes or acrylic resin varnishes are not required in principle. However, they may be used depending upon the purpose of inhibiting fouling.

The antifouling agent of this invention is embodied in various forms. Preferably, the solids of the antifouling agent contain at least 0.5% by weight of units derived from the triorganotin compound ($R_3SnX$).

The antifouling agent of this invention has the following characteristics. Firstly, the antifouling agent has long-term storage stability, and does not substantially undergo changes with time such as gellation. Its storage stability does not change even when it contains a copper compound such as cuprous oxide. This effect is not observed with conventional triorganotin-containing polymer-type antifouling agents having —COOSnR$_3$ in the molecule. Secondly, since the triorganotin compound is introduced and fixed into and to the polymer by a coordination bond, its toxicity to the human body is markedly reduced as compared with the conventional triorganotin compound monomer-type antifouling agents, and there is no likelihood of causing hazards to the operators. Thirdly, when the antifouling agent is coated on a substrate to be protected from fouling, a tough coated film having strong adhesion is formed and therefore a protective film having excellent antifouling properties and physical and chemical resistance is obtained. Fourthly, since the antifouling agent is a copolymer having a hydrophilic residue of a nitrogen-containing compound, it has properties as a soluble matrix.

Thus, when it is dipped in sea water, the surface of the coated film is always renewed and its antifouling property can be maintained over a long period of time. Hence, by varying the proportions of the N-coordinated-triorganotin-containing structural units and the co-monomer units in the polymer of this invention according to the antifouling purpose, the antifouling agent can be adjusted over a wide range from the insoluble matrix type to the soluble matrix type. Furthermore, the present invention has the advantage that an antifouling agent containing a triphenyltin-containing copolymer which is effective against algae can be produced.

The antifouling agent of this invention is especially advantageously used to protect an object to be in contact with sea water, such as bottoms of ships made of steel, wood and reinforced plastics, fishing nets, marine structures, sea water conduits, etc. It can also be applied to the protection of articles and structures which are liable to undergo damage by fouling organisms because of their long-term contact with river water, lake water and other waters.

The following examples and test examples illustrate the present invention. All percents and parts in these examples are by weight.

The molecular weight denotes a weight average molecular weight determined by the GPC method (measuring instrument: HITACHI 635, Column: Shodex A-804).

EXAMPLE 1

A 500 ml three-necked flask equipped with a thermometer, reflux condenser and stirrer was charged with 32 g of N-vinyl-N-methylacetamide, 60 g of methyl methacrylate, 10 g of octyl acrylate and 200 g of xylene, and 0.5 g of azobisisobutyronitrile was added. The inside of the flask was purged with nitrogen gas. With stirring, the temperature of the inside of the flask was raised to 75° C. Then, with stirring at the same temperature, 0.2 g of azobisisobutyronitrile (AIBN) was added three times at intervals of 3 hours, and the polymerization was carried out for a total time of 12 hours to form a nitrogen-containing copolymer solution. To the solution was added 98 g of tributyltin chloride, and the mixture was stirred at 50° C. for 2 hours to perform addition reaction to obtain a solution of an N-coordinated-tributyltin-containing copolymer having a molecular weight of 96,000 (to be designated as copolymer solution [A-1]). This copolymer solution was directly used as an antifouling agent.

The copolymer solution was dissolved in deuteriumbenzene to a concentration of 20% by weight, and the $^{119}$Sn chemical shift was measured by a $^{119}$Sn NMR measuring instrument (JEOL-FX 100 made by Nitto Electronics Co., Ltd.). The chemical shift value of this copolymer using tetramethyltin as a standard was +103 ppm. The chemical shift value of tributyltin chloride, measured in the same way, was +145 ppm. It was found therefore that shifting to a higher magnetic field side by 42 ppm occurred.

When the copolymer solution was analyzed for characteristic absorptions in an IR spectrum, it was found that the absorption of tributyltin chloride at 595 cm$^{-1}$ due to the Sn-C anti-symmetric vibration shifted to 602 cm$^{-1}$, and the carbonyl absorption at 1650 cm$^{-1}$ in the amide group of N-vinyl-N-methyl-acetamide shifted to 1610 cm$^{-1}$.

EXAMPLES 2 TO 17

By the same procedure as in Example 1, the polymerization components, solvent and catalyst shown in Table I were charged into a reactor, and polymerization was carried out to prepare a nitrogen-containing copolymer solution. Then, addition reaction was carried out by adding the triorganotin halide to form N-coordinated-triorganotin-containing copolymer solutions (to be referred to as copolymer solutions [A-2] to [A-17]). These copolymer solutions [A-2] to [A-17] were directly used as antifouling agents.

The various data are shown in Table I.

TABLE I

| Example | Monomers used in the copolymerization | Amount (g) | Solvent | Amount (g) | Catalyst | Polymerization conditions | $R_3SnX$ | Amount (g) | Antifouling agent (copolymer solution) Designation | Molecular weight |
|---|---|---|---|---|---|---|---|---|---|---|
| 2 | N—vinyl diethylamine<br>Methyl methacrylate<br>Octyl acrylate | 36<br>62<br>20 | Methyl ethyl ketone | 200 | AIBN | 75° C./<br>20 hrs | $Pr_3SnCl$ | 82 | [A-2] | 27,000 |
| 3 | N—vinylmorpholine<br>Butyl acrylate<br>Octyl acrylate | 34<br>40<br>10 | Methyl ethyl ketone | 200 | AIBN | 75° C./<br>20 hrs | $Ph_3SnCl$ | 116 | [A-3] | 49,000 |
| 4 | N—vinylpyrrolidone<br>Butyl acrylate | 40<br>58 | Xylene | 200 | AIBN | 75° C./<br>10 hrs | $Ph_3SnCl$ | 102 | [A-4] | 71,000 |
| 5 | N—vinylpyrrolidone<br>Methyl methacrylate<br>Styrene | 36<br>40<br>20 | Xylene<br>Methyl isobutyl ketone | 100<br>100 | BPO | 95° C./<br>10 hrs | $Bu_3SnCl$ | 104 | [A-5] | 165,000 |
| 6 | N—vinylphenylethylamine<br>Ethyl acrylate<br>Tributyltin methacrylate | 32<br>56<br>20 | Xylene<br>iso-Butanol | 100<br>100 | AIBN | 75° C./<br>20 hrs | $Bu_3SnBr$ | 92 | [A-6] | 32,000 |
| 7 | N—vinylcarbazole<br>Methyl methacrylate<br>Octyl acrylate | 50<br>40<br>26 | Xylene | 100 | BPO | 95° C./<br>10 hrs | $Bu_3SnCl$ | 84 | [A-7] | 38,000 |
| 8 | N—vinylsuccinimide<br>Acrylonitrile<br>Octyl methacrylate | 40<br>40<br>16 | Ethyl Cellosolve<br>Methyl ethyl ketone | 100<br>100 | AIBN | 75° C./<br>20 hrs | $Ph_3SnCl$ | 104 | [A-8] | 54,000 |
| 9 | N,N—diethylacrylamine<br>Methyl methacrylate<br>Styrene<br>Octyl acrylate | 24<br>72<br>14<br>20 | Xylene<br>Ethyl Cellosolve | 50<br>150 | AIBN | 75° C./<br>20 hrs | $Ph_3SnBr$ | 70 | [A-9] | 9,800 |

TABLE I-continued

| Example | Monomers used in the copolymerization | Amount (g) | Solvent | Amount (g) | Catalyst | Polymerization conditions | $R_3SnX$ | Amount (g) | Antifouling agent (copolymer solution) Designation | Molecular weight |
|---|---|---|---|---|---|---|---|---|---|---|
| 10 | p-Dimethylaminostyrene | 40 | Xylene | 275 | AIBN | 75° C./10 hrs | $Ph_3SnCl$ | 78 | [A-10] | 272,200 |
| | Methyl methacrylate | 72 | | | | | | | | |
| | Octyl acrylate | 10 | | | | | | | | |
| 11 | N,N—dimethylaminoacrylamide | 44 | iso-Butanol | 200 | BPO | 95° C./10 hrs | $Bu_3SnCl$ | 56 | [A-11] | 183,000 |
| | Methyl methacrylate | 78 | | | | | | | | |
| | Styrene | 17 | | | | | | | | |
| | Methacrylic acid | 5 | | | | | | | | |
| 12 | Methacryloyl morpholine | 40 | Xylene | 100 | AIBN | 75° C./10 hrs | $Ph_3SnCl$ | 88 | [A-12] | 62,000 |
| | Methyl methacrylate | 40 | iso-Butanol | 100 | | | | | | |
| | Octyl vinyl ether | 32 | | | | | | | | |
| 13 | N,N—diethylaminoethyl methacrylate | 54 | Xylene | 200 | AIBN | 75° C./10 hrs | $Bu_3SnCl$ $Ph_3SnCl$ | 34 62 | [A-13] | 59,000 |
| | Styrene | 16 | | | | | | | | |
| | Octyl acrylate | 32 | | | | | | | | |
| 14 | β-Pyrrolidinoethyl methacrylate | 34 | Xylene iso-Butanol | 100 100 | AIBN | 75° C./15 hrs | $Ph_3SnCl$ | 66 | [A-14] | 27,000 |
| | Methyl acrylate | 60 | | | | | | | | |
| | Octyl acrylate | 40 | | | | | | | | |
| 15 | N,N—dimethylaminoethyl vinyl ether | 34 | Xylene n-Butanol | 100 100 | AIBN | 75° C./15 hrs | $Ph_3SnCl$ | 108 | [A-15] | 101,000 |
| | Styrene | 44 | | | | | | | | |
| | Butyl acrylate | 14 | | | | | | | | |
| 16 | 4-Vinylpyridine | 44 | Tetrahydrofuran | 50 | AIBN | 75° C./15 hrs | $Bu_3SnCl$ | 98 | [A-16] | 44,000 |
| | Butyl acrylate | 46 | | | | | | | | |
| | Octyl vinyl ether | 12 | Xylene | 150 | | | | | | |
| 17 | N,N—dimethylaminoethyl acrylate | 26 | Xylene iso-Butanol | 100 100 | AIBN | 75° C./15 hrs | $Ph_3SnCl$ | 64 | [A-17] | 88,000 |
| | Styrene | 20 | | | | | | | | |
| | Butyl acrylate | 66 | | | | | | | | |
| | Tributyltin acrylate | 24 | | | | | | | | |

In Table I and subsequent tables, the following abbreviations are used:
AIBN: azobisisobutyronitrile
BPO: benzoyl peroxide
Ph: phenyl group
Bu: Butyl group
Pr: propyl group

EXAMPLE 18

The same reactor as used in Example 1 was charged with 30 g of N-vinylpyrrolidone, 104 g of triphenyltin chloride and 200 g of xylene, and the mixture was stirred at 50° C. for 2 hours to form an N-vinylpyrrolidone/triphenyltin chloride adduct. Then, 50 g of butyl acrylate, 16 g of octyl acrylate and 0.5 g of benzoyl peroxide were added, and with stirring, the mixture was heated to 75° C. At this temperature, 0.2 g of benzoyl peroxide was added three times at intervals of 3 hours, and the polymerization reaction was carried out for a total of 12 hours to give an N-coordinated-triphenyltin-containing copolymer solution having a molecular weight of 77,000 (to be referred to as a copolymer solution [A-18]). This copolymer solution was used directly as an antifouling agent.

Using this copolymer solution, the $^{119}Sn$ chemical shift was measured by the same method as described in Example 1, and a value of −73.2 ppm was obtained. The chemical shift of triphenyltin chloride measured in the same way was −42.9 ppm. It was found that there was a shift of 30.3 ppm to a higher magnetic field side.

The copolymer solution was analyzed for characteristic absorptions in an IR spectrum. It was found that as a result of triphenyltin chloride being coordinated with the nitrogen atom in the cyclic amide, the absorption of the carbonyl of the amide group of N-vinylpyrrolidone at 1690 cm$^{-1}$ shifted to 1630 cm$^{-1}$.

EXAMPLES 19 TO 27

By the same procedure as in Example 18, a reactor was charged with the nitrogen-containing unsaturated compound, the triorganotin compound and the solvent shown in Table II to perform addition reaction. Thereafter the comonomer component and the catalyst shown in Table II were added to perform polymerization. Thus, solutions of N-coordinated-triorganotin-containing copolymers (copolymer solutions [A-19] to [A-27]) were obtained. These copolymer solutions were directly used as antifouling agents.

The various data are shown in Table II.

TABLE II

| Example | Monomers used in the copolymerization Compound | Amount (g) | Solvent Compound | Amount (g) | Catalyst | Polymerization conditions | Antifouling agent of the invention (copolymer solution) Designation | Molecular weight |
|---|---|---|---|---|---|---|---|---|
| 19 | N—vinyldimethylamine | 24 | Methyl ethyl ketone | 200 | AIBN | 75° C./20 hrs | [A-19] | 31,000 |
| | $Bu_3SnCl$ | 96 | | | | | | |
| | Acrylonitrile | 30 | | | | | | |
| | Butyl acrylate | 50 | | | | | | |

TABLE II-continued

| Example | Monomers used in the copolymerization Compound | Amount (g) | Solvent Compound | Amount (g) | Catalyst | Polymerization conditions | Antifouling agent of the invention (copolymer solution) Designation | Molecular weight |
|---|---|---|---|---|---|---|---|---|
| 20 | N—vinyl-N—phenylacetamide<br>Ph₃SnCl<br>Methyl methacrylate<br>Octyl acrylate | 36<br>74<br>38<br>52 | iso-Butanol | 200 | BPO | 95° C./<br>12 hrs | [A-20] | 56,000 |
| 21 | p-Vinylpiperidine<br>Bu₃SnCl<br>Butyl acrylate<br>Octyl vinyl ether | 26<br>54<br>80<br>40 | Xylene<br>Methyl iso-<br>butyl ketone | 150<br>50 | BPO | 95° C./<br>15 hrs | [A-21] | 51,000 |
| 22 | N,N—diethylaminoethyl vinyl sulfide<br>Ph₃SnCl<br>Butyl vinyl ether | 52<br>108<br>40 | iso-Butanol<br>Xylene | 150<br>50 | AIBN | 75° C./<br>10 hrs | [A-22] | 63,000 |
| 23 | Morpholinoethyl acrylate<br>Ph₃SnCl<br>Ethyl acrylate<br>Octyl acrylate | 54<br>90<br>26<br>30 | Xylene | 200 | AIBN | 75° C./<br>12 hrs | [A-23] | 72,000 |
| 24 | N,N—diethyl methacrylate<br>Bu₃SnBr<br>Styrene<br>Butyl acrylate | 30<br>74<br>16<br>80 | Ethyl Cellosolve<br>Xylene | 100<br>100 | BPO | 95° C./<br>10 hrs | [A-24] | 138,000 |
| 25 | N—vinylpyrrolidone<br>Ph₃SnCl<br>Methyl methacrylate<br>Butyl acrylate | 28<br>62<br>60<br>50 | Xylene | 200 | AIBN | 75° C./<br>10 hrs | [A-25] | 55,000 |
| 26 | N—vinyl-N—methylacetamide<br>Bu₃SnCl<br>Methyl methacrylate<br>Tributyltin methacrylate | 26<br>82<br>72<br>20 | Ethyl Cellosolve<br>Xylene | 100<br>100 | AIBN | 75° C./<br>10 hrs | [A-26] | 157,000 |
| 27 | p-Aminostyrene<br>Ph₃SnCl<br>Butyl vinyl ether<br>Octyl acrylate<br>Maleic anhydride | 32<br>98<br>40<br>25<br>5 | iso-Butanol<br>Methyl ethyl ketone | 100<br>100 | AIBN | 75° C./<br>15 hrs | [A-27] | 42,000 |

REFERENTIAL EXAMPLE

A reactor was charged with 120 g of triphenyltin methacrylate, 64 g of octyl acrylate, 16 g of methyl methacrylate and 200 g of xylene. After dissolving them well, 0.8 g of azobisisobutyronitrile was added. With stirring, the polymerization was carried out at 75° C. for 3 hours. There was obtained a triphenyltin-containing copolymer solution having a molecular weight of 78,000 (the copolymer solution of Referential Example).

EXAMPLES 28 TO 54

Antifouling paints for ship's bottoms in accordance with this invention were prepared by adding the ingredients shown in Table III to each of the N-coordinated-triorganotin-containing copolymer solutions obtained in Examples 1 to 27.

The results are shown in Table III.

TABLE III

| Blending ingredients | 28 | 29 | 30 | 31 | 32 | 33 | 34 | 35 | 36 | 37 | 38 | 39 | 40 | 41 |
|---|---|---|---|---|---|---|---|---|---|---|---|---|---|---|
| Copolymer solution [A-1] | 40 | | | | | | | | | | | | | |
| Copolymer solution [A-2] | | 40 | | | | | | | | | | | | |
| Copolymer solution [A-3] | | | 40 | | | | | | | | | | | |
| Copolymer solution [A-4] | | | | 40 | | | | | | | | | | |
| Copolymer solution [A-5] | | | | | 40 | | | | | | | | | |
| Copolymer solution [A-6] | | | | | | 40 | | | | | | | | |
| Copolymer solution [A-7] | | | | | | | 40 | | | | | | | |
| Copolymer solution [A-8] | | | | | | | | 40 | | | | | | |
| Copolymer solution [A-9] | | | | | | | | | 40 | | | | | |
| Copolymer solution [A-10] | | | | | | | | | | 40 | | | | |
| Copolymer solution [A-11] | | | | | | | | | | | 40 | | | |
| Copolymer solution [A-12] | | | | | | | | | | | | 40 | | |
| Copolymer solution [A-13] | | | | | | | | | | | | | 40 | |
| Copolymer solution [A-14] | | | | | | | | | | | | | | 40 |
| Cuprous oxide | 40 | 30 | 40 | 40 | 40 | 40 | 40 | 40 | 40 | 40 | 40 | 40 | 40 | 40 |
| Cuprous rhodanate | | 10 | | | | | | | | | | | | |
| (Bu₃Sn)₂O | | | | | | | | | 2 | | | | | |
| Ph₃SnOH | | | | | | | | | | | 1 | | | |
| Zinc oxide | | | | | | | 2 | | | 1 | | | | |
| Titanium oxide | | | 5 | | 5 | 1 | | | | | | | | |
| Red iron oxide | 5 | 5 | | 5 | | 5 | 10 | 5 | 5 | 5 | 5 | 5 | 5 | 5 |
| Talc | 5 | 5 | 5 | 5 | 5 | 4 | 8 | 5 | 5 | 4 | 5 | 5 | 5 | 5 |
| Xylene | 15 | 10 | 10 | 10 | 15 | 10 | 10 | 10 | 5 | 20 | 20 | 10 | 10 | 5 |

TABLE III-continued

| Blending ingredients | 42 | 43 | 44 | 45 | 46 | 47 | 48 | 49 | 50 | 51 | 52 | 53 | 54 |
|---|---|---|---|---|---|---|---|---|---|---|---|---|---|
| Copolymer solution [A-15] | 40 | | | | | | | | | | | | |
| Copolymer solution [A-16] | | 40 | | | | | | | | | | | |
| Copolymer solution [A-17] | | | 40 | | | | | | | | | | |
| Copolymer solution [A-18] | | | | 40 | | | | | | | | | |
| Copolymer solution [A-19] | | | | | 40 | | | | | | | | |
| Copolymer solution [A-20] | | | | | | 40 | | | | | | | |
| Copolymer solution [A-21] | | | | | | | 40 | | | | | | |
| Copolymer solution [A-22] | | | | | | | | 40 | | | | | |
| Copolymer solution [A-23] | | | | | | | | | 40 | | | | |
| Copolymer solution [A-24] | | | | | | | | | | 40 | | | |
| Copolymer solution [A-25] | | | | | | | | | | | 40 | | |
| Copolymer solution [A-26] | | | | | | | | | | | | 40 | |
| Copolymer solution [A-27] | | | | | | | | | | | | | 40 |
| Cuprous oxide | 40 | 30 | 40 | 40 | 40 | 40 | 40 | 40 | 40 | 40 | 40 | 40 | 40 |
| Cuprous rhodanate | | 10 | | | | | | | | | | | |
| $(Bu_3Sn)_2O$ | | | | | | | | | | | | | |
| $Ph_3SnOH$ | | | 2 | | | | | | | | | | |
| Zinc oxide | 2 | | | | | | | 1 | | | | | 2 |
| Titanium oxide | | | | | | | | | 5 | | | | |
| Red iron oxide | 5 | 5 | 5 | 5 | 5 | 5 | 5 | | 5 | 5 | 5 | 5 | 5 |
| Talc | 4 | 5 | 5 | 5 | 5 | 5 | 5 | 5 | 5 | 5 | 5 | 5 | 4 |
| Xylene | 10 | 10 | 10 | 10 | 10 | 10 | 10 | 10 | 10 | 15 | 10 | 15 | 10 |

I. Adhesion test

Each of the antifouling agents obtained in Examples 1 to 27 was brush-coated to a thickness of 60 microns on a sand-blasted mild steel test panel (25×8×0.5 cm in size), and dried at room temperature for 3 days. The surface of the coated film was cross-cut (perpendicular crossing with 1 mm width; 100 squares), and a peel test was carried out by using an adhesive tape. The cross-cut squares in all of the test panels remained unpeeled, thus showing good adhesion.

Each of the antifouling agents obtained in Examples 1 to 27 was coated to a film thickness of 100 microns on the same test panel as above, and dried. The coated panel was dipped for 3 months in artificial sea water, and the state of the coated film was observed with the naked eye. No peel or swelling was observed in any of the test plates.

II. Antifouling test (clear coating)

Each of the antifouling agents obtained in Examples 1 to 27 (copolymer solutions [A-1] to [A-27]) was coated on both surfaces of a rigid vinyl chloride resin plate, 17×9×0.3 cm, to a dry film thickness of about 150 microns. The coated plate was dipped in sea water by suspending it from a sea raft at Owase Bay, Mie Prefecture, Japan for 6 months, and their state of fouling was observed. The results are shown in Table IV.

The symbols in the following tables show the following ratings.

O: No adhesion of marine animals and plants
Δ: Marine animals and plants adhered to less than 5% of the area of the coated film.
X: Marine animals and plants adhered to 5 to 20% of the area of the coated film.
XX: Marine animals and plants adhered to 20 to 50% of the area of the coated surface.
XXX: Marine animals and plants adhered to more than 50% of the coated surface.

TABLE IV

| Antifouling agent of Example | Period | | |
|---|---|---|---|
| | 1 Month | 3 Months | 6 Months |
| 1 | | | |
| 2 | | | Δ |
| 3 | | | |
| 4 | | | |
| 5 | | | |
| 6 | | | X |
| 7 | | | Δ |
| 8 | | | |
| 9 | | | X |
| 10 | | | Δ |
| 11 | | | |
| 12 | | | |
| 13 | | | Δ |
| 14 | | | |
| 15 | | | |
| 16 | | | |
| 17 | | | |
| 18 | | | |
| 19 | | | |
| 20 | | | Δ |
| 21 | | | X |
| 22 | | | |
| 23 | | | |
| 24 | | | Δ |
| 25 | | | X |
| 26 | | | |
| 27 | | | |
| Blank (rigid vinyl chloride resin plate) | X | XXX | XXX |

III. Antifouling test (ship bottom paint)

Each of the ship bottom antifouling paints of the invention obtained in Examples 28 to 54 was coated on both surfaces of a rigid vinyl chloride resin plate having a size of 17×9×0.3 cm to a dry film thickness of about 200 microns. The coated plate was dipped in sea water by suspending it from a sea raft in Owase Bay, Mie Prefecture, Japan for 12 months, and their state of fouling was regularly observed.

The results are shown in Table V.

TABLE V

| Antifouling paint of Example | Period | | |
|---|---|---|---|
| | 4 Months | 8 Months | 12 Months |
| 28 | | | |
| 29 | | | Δ |
| 30 | | | |
| 31 | | | |
| 32 | | | |

TABLE V-continued

| Antifouling paint of Example | Period | | |
|---|---|---|---|
| | 4 Months | 8 Months | 12 Months |
| 33 | | | Δ |
| 34 | | | Δ |
| 35 | | | |
| 36 | | | X |
| 37 | | | Δ |
| 38 | | | Δ |
| 39 | | | |
| 40 | | | |
| 41 | | | X |
| 42 | | | |
| 43 | | | |
| 44 | | | Δ |
| 45 | | | |
| 46 | | | Δ |
| 47 | | | Δ |
| 48 | | | X |
| 49 | | | |
| 50 | | | |
| 51 | | | |
| 52 | | | Δ |
| 53 | | | |
| 54 | | | |
| Blank (rigid vinyl chloride resin plate) | XXX | — | — |

IV. Antifouling test (fishing net)

One hundred parts of each of the antifouling agents obtained in Examples 1 to 27 (copolymer solutions [A-1] to [A-27]) was diluted with 200 parts of xylene. A polyethylene fishing net (30×40 cm in size; 24 plies, 8 knots) was dipped in each of the diluted solutions, and taken out several minutes later. The fishing net was dried in the air and mounted on an iron frame. The amount of the diluted solution coated was about 20% based on the weight of the fishing net. The net was dipped in sea water by suspending it from a sea raft for 3 months in Owase Bay, Mie Prefecture, Japan, and its state of fouling was observed every month. The results are shown in Table VI.

TABLE VI

| Antifouling agent of Example | Period | | |
|---|---|---|---|
| | 1 Month | 2 Months | 3 Months |
| 1 | | | |
| 2 | | | Δ |
| 3 | | | |
| 4 | | | |
| 5 | | | |
| 6 | | | |
| 7 | | | |
| 8 | | | |
| 9 | | | Δ |
| 10 | | | |
| 11 | | | |
| 12 | | | Δ |
| 13 | | | |
| 14 | | | Δ |
| 15 | | | |
| 16 | | | |
| 17 | | | |
| 18 | | | |
| 19 | | | Δ |
| 20 | | | |
| 21 | | | Δ |
| 22 | | | |
| 23 | | | |
| 24 | | | |
| 25 | | | |
| 26 | | | |
| 27 | | | |
| Blank (polyethylene fishing net) | XX | XXX | — |

V. Storage stability test (antifouling agent)

Each of the antifouling agents (copolymer solutions [A-1] to [A-27]) obtained in Examples 1 to 27 was put in a 100 ml glass bottle, and stored for three months in an oven at 50° C. After the lapse of a predetermined period of time, it was taken out, and observed for changes with time. The same test was conducted on the copolymer solution of Referential Example.

The results are shown in Table VII.

The symbols in the table show the following ratings (the sample applies to the subsequent table).

A: No change in viscosity was noted in comparision with the antifouling agent or antifouling paint immediately after preparation.

B: A slight increase in viscosity was noted in comparison with the antifouling agent or antifouling paint immediately after preparation.

C: A marked increase in viscosity was noted in comparison with the antifouling agent or antifouling paint immediately after preparation.

D: The antifouling agent or antifouling paint gelled.

TABLE VII

| Antifouling agent of Example | Storage period | | | |
|---|---|---|---|---|
| | 1 Week | 1 Month | 2 Months | 3 Months |
| 1 | A | A | A | A |
| 2 | A | A | A | B |
| 3 | A | A | A | B |
| 4 | A | A | A | A |
| 5 | A | A | A | A |
| 6 | A | A | A | B |
| 7 | A | A | A | A |
| 8 | A | A | A | A |
| 9 | A | A | A | B |
| 10 | A | A | A | A |
| 11 | A | A | A | A |
| 12 | A | A | A | A |
| 13 | A | A | B | C |
| 14 | A | A | A | B |
| 15 | A | A | A | A |
| 16 | A | A | A | B |
| 17 | A | A | A | B |
| 18 | A | A | A | A |
| 19 | A | A | A | B |
| 20 | A | A | A | B |
| 21 | A | A | A | A |
| 22 | A | A | A | B |
| 23 | A | A | A | B |
| 24 | A | A | A | A |
| 25 | A | A | A | A |
| 26 | A | A | A | A |
| 27 | A | A | A | A |
| Copolymer solution of Referential Example | D | — | — | — |

VI. Storage stability test (antifouling paint)

Each of the antifouling paints obtained in Examples 28 to 54 was put in a 100 ml. glass bottle, and stored in an oven at 50° C. for 3 weeks. It was taken out after the passage of a predetermined period of time, and observed for changes with time. The results are shown in Table VIII.

TABLE VIII

| Antifouling paint of Example | Storage period | | |
|---|---|---|---|
| | 1 Week | 2 Weeks | 3 Weeks |
| 28 | A | A | A |
| 29 | A | A | B |
| 30 | A | A | A |
| 31 | A | A | A |
| 32 | A | A | A |
| 33 | A | A | B |
| 34 | A | A | A |

TABLE VIII-continued

| | | | |
|---|---|---|---|
| 35 | A | A | A |
| 36 | A | A | B |
| 37 | A | A | B |
| 38 | A | A | A |
| 39 | A | A | A |
| 40 | A | A | B |
| 41 | A | A | A |
| 42 | A | A | A |
| 43 | A | A | A |
| 44 | A | A | B |
| 45 | A | A | B |
| 46 | A | A | B |
| 47 | A | A | A |
| 48 | A | A | A |
| 49 | A | A | A |
| 50 | A | A | B |
| 51 | A | A | A |
| 52 | A | A | A |
| 53 | A | A | A |
| 54 | A | A | A |
| Antifouling paint of Referential Example(*) | D(**) | — | — |

(Note) Formulation of the antifouling paint of Referential Example(*)

| | |
|---|---|
| Copolymer solution of Referential Example | 40 parts |
| Cuprous oxide | 40 parts |
| Red iron oxide | 5 parts |
| Talc | 5 parts |
| Xylene | 15 parts |

(**) Gelled in 3 days.

What is claimed is:

1. An antifouling agent comprising as an antifouling copolymer containing
    (a) 10 to 80% by weight of at least one kind of N-coordinated-triorganotin-containing recurring units of the formula

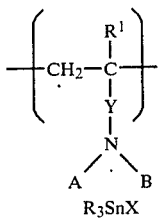
R₃SnX (Ia)

wherein $R^1$ represents a hydrogen atom, a methyl group or a halogen atom; (i) when A and B independently from each other represent a hydrogen atom, an alkyl group having 1 to 18 carbon atoms, a cycloalkyl group, an aryl group, an aralkyl group, a hydroxyalkyl group having 2 to 4 carbon atoms or a group of the formula

in which $R^3$ represents an alkyl group having 1 to 18 carbon atoms, or an aryl group, Y represents a bond, an alkylene group having 1 to 12 carbon atoms, a phenylene group, a group of the formula

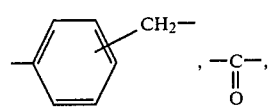

or a group of the formula

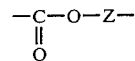

or —O—Z— in which Z represents an alkylene group having 2 to 12 carbon atoms, or (ii) when A and B are bonded to each other together with the nitrogen atom to which they are bonded, to form a 5- or 6-membered heterocyclic ring, Y represents a bond or a group of the formula

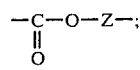

groups R are identical or different and each represents an alkyl group having 1 to 8 carbon atoms or an aryl group; and X represents a halogen atom, or

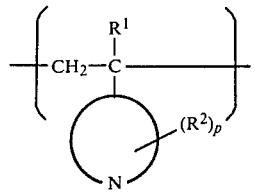 (Ib)

R₃SnX wherein $R^1$, R and X are as defined as in regard to formula (Ia); $R^2$ represents a hydrogen atom, a methyl group, an ethyl group or a halogen atom; p is an integer of from 1 to 4; the symbol

represents a 5- or 6-membered heterocyclic ring bonded through a ring-member atom other than the nitrogen atom to the carbon atom to which $R^1$ is bonded, and
    (b) 90 to 20% by weight of comonomer recurring units derived from at least one ethylenic vinyl compound as a comonomer selected from the group consisting of acrylic compounds of the formula

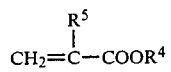

wherein $R^4$ represents a hydrogen atom, a substituted or unsubstituted hydrocarbon group having 1 to 20 carbon atoms, and $R^5$ represents a hydrogen or a methyl group;

vinyl compounds having a functional group of the formula

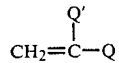

wherein Q represents a halogen atom, —CN, —OR* or —OCOR* in which R* represents a substituted or unsubstituted hydrocarbon group having 1 to 20 carbon atoms, and Q' represents a hydrogen atom, a halogen atom or a methyl group;
and styrene, said percent by weight being based on the total weight of these two kinds of recurring units.

2. The antifouling agent of claim 1 wherein in formula (Ia), A and B, independently from each other, represents a hydrogen atom, an alkyl group having 1 to 8 carbon atoms, a 5- or 6-membered cycloalkyl group, a phenyl group, a naphthyl group, a benzyl group, an α-penethyl group, a β-phenethyl group, a hydroxyalkyl group having 2 or 3 carbon atoms, or an acyl group of the formula

in which $R^{31}$ represents an alkyl group having 1 to 8 carbon atoms, a phenyl group, a tolyl group or a naphthyl group.

3. The antifouling agent of claim 1 wherein in formula (Ia), A and B are bonded to each other and, together with the nitrogen atom to which they are bonded, represent a 5- or 6-membered heterocyclic ring containing no ring-member hetero atom other than the nitrogen atom, or a 5- or 6-membered heterocyclic ring containing an oxygen or sulfur atom as a ring-member hetero atom in addition to the nitrogen atom.

4. The antifouling agent of claim 1 or 3 wherein in formula (Ia), the group

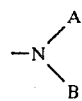

is an amino group, a dialkylamino group, an N-acyl-N-alkylamino group, an N-alkyl-N-arylamino group, or an N-acyl-N-arylamino group.

5. The antifouling agent of claim 1 or 4 wherein in formula (Ia), the group

represents a 5-membered heterocyclic ring containing no ring-member hetero atom other than the nitrogen atom, or a 6-membered heterocyclic ring containing an oxygen atom as a ring-member hetero atom in addition to the nitrogen atom.

6. The antifouling agent of claim 1 wherein in formula (Ib), the symbol

represents a 6-membered heterocyclic ring containing no ring-member hetero atom other than the nitrogen atom.

7. The antifouling agent of claim 1 wherein the three R groups represent the same group.

8. The antifouling agent of claim 1 wherein X is a chlorine atom.

9. The antifouling agent of claim 1 or 10 wherein the substantially linear triorganotin-containing copolymer is composed substantially of the N-coordinated-triorganotin-containing recurring units and the comonomer recurring units.

10. The antifouling agent of claim 1 wherein the substantially linear triorganotin-containing copolymer has a weight average molecular weight of about 5,000 to about 500,000.

* * * * *